United States Patent [19]

Gorski et al.

[11] Patent Number: 4,741,437

[45] Date of Patent: * May 3, 1988

[54] SELF-CONTAINED INDICATOR DEVICE

[75] Inventors: Theodore W. Gorski; Richard F. Wallin, both of Perrysburg, Ohio

[73] Assignee: North American Science Associates Inc., Northwood, Ohio

[*] Notice: The portion of the term of this patent subsequent to Apr. 8, 2003 has been disclaimed.

[21] Appl. No.: 748,301

[22] Filed: Jun. 24, 1985

Related U.S. Application Data

[63] Continuation-in-part of Ser. No. 462,516, Jan. 31, 1983, Pat. No. 4,580,682.

[51] Int. Cl.$^4$ .................. B65D 25/08; B65D 81/32
[52] U.S. Cl. ..................... 206/222; 206/569; 435/31; 436/1
[58] Field of Search ............... 206/216, 219, 221, 222, 206/459, 569; 220/258; 222/83; 422/58; 436/1; 435/31, 296

[56] References Cited

U.S. PATENT DOCUMENTS

| | | | |
|---|---|---|---|
| 3,134,725 | 5/1964 | Brook et al. | 435/296 |
| 3,255,926 | 6/1966 | Modderno | 222/136 |
| 3,378,168 | 4/1968 | Hilderbrandt | 222/83 |
| 3,402,855 | 7/1968 | Schroeder et al. | 222/83 |
| 3,440,144 | 4/1969 | Andersen | 435/3 F |
| 3,613,955 | 10/1971 | Wetherell | 222/83 |
| 3,661,717 | 5/1972 | Nelson | 435/31 |
| 3,762,540 | 10/1973 | Baumann et al. | 206/219 |
| 3,968,872 | 7/1976 | Cavazza | 206/222 |
| 4,136,775 | 1/1979 | Zaltsman | 206/219 |
| 4,252,904 | 2/1981 | Nelson et al. | 435/296 |
| 4,267,925 | 5/1981 | Crankshaw et al. | 206/221 |
| 4,291,122 | 9/1981 | Orelski | 435/296 |
| 4,304,869 | 12/1981 | Dyke | 435/296 |
| 4,311,793 | 1/1982 | Halleck | 435/31 |
| 4,314,030 | 2/1982 | Habich | 435/296 |
| 4,348,209 | 9/1982 | Murtaugh et al. | 55/158 |
| 4,355,113 | 10/1982 | Mennen | 435/295 |
| 4,416,984 | 11/1983 | Wheeler, Jr. | 435/31 |
| 4,528,268 | 7/1985 | Anderson et al. | 435/296 |
| 4,580,682 | 4/1986 | Gorski et al. | 206/569 |

FOREIGN PATENT DOCUMENTS 0078112 5/1983 European Pat. Off. .
2476607 8/1981 France .

*Primary Examiner*—Stephen Marcus
*Attorney, Agent, or Firm*—Emch, Schaffer, Schaub & Porcello Co.

[57] ABSTRACT

The application discloses a test vial including a test article for immersion into a fluid medium, a sealed chamber which contains the fluid medium, and an open chamber which is external to the sealed chamber and which supports the test article. The sealed and open chambers define a barrier which isolates the fluid medium from the test article. The open chamber is covered by a closure. Retaining means are positioned on the closure and cooperatively support the closure in a first position and cooperatively receive the closure in a second position. The closure has a means for penetrating the barrier and for injecting the test article into the fluid medium when the closure is moved from the first position to the second position while maintaining the sealed chamber in a sealed condition upon movement of the closure from the first position to the second position.

6 Claims, 6 Drawing Sheets

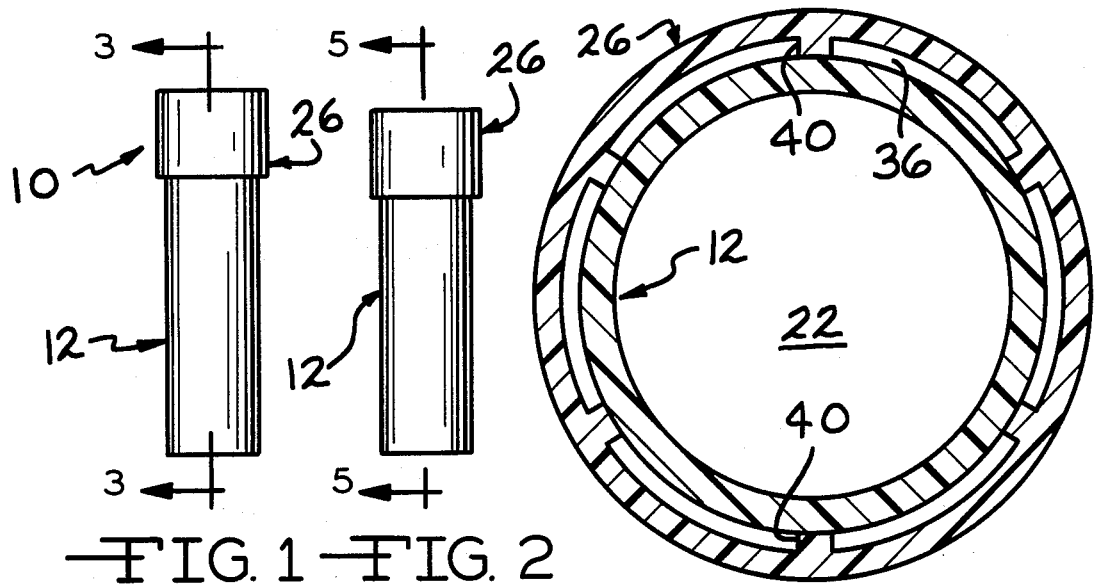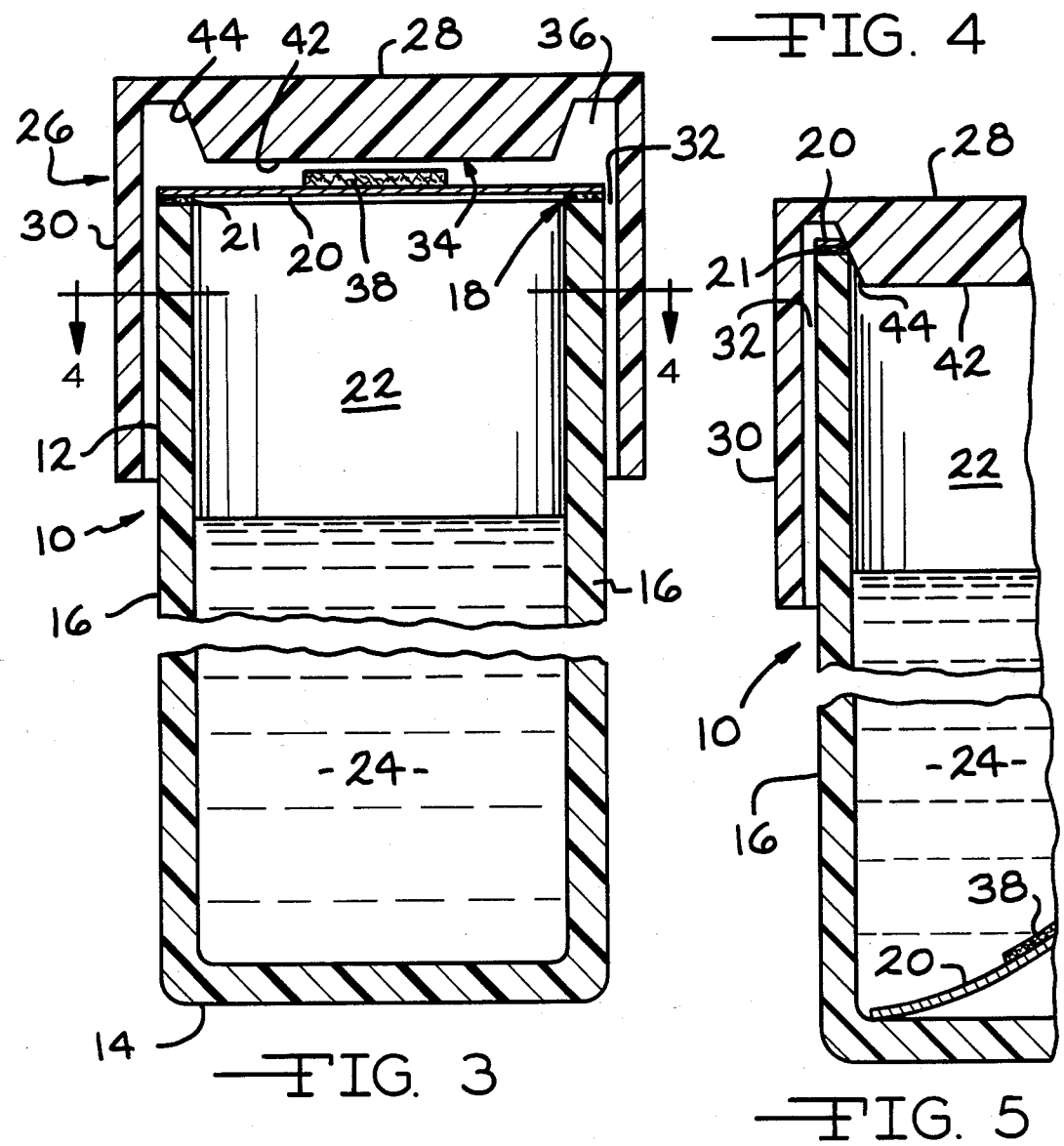

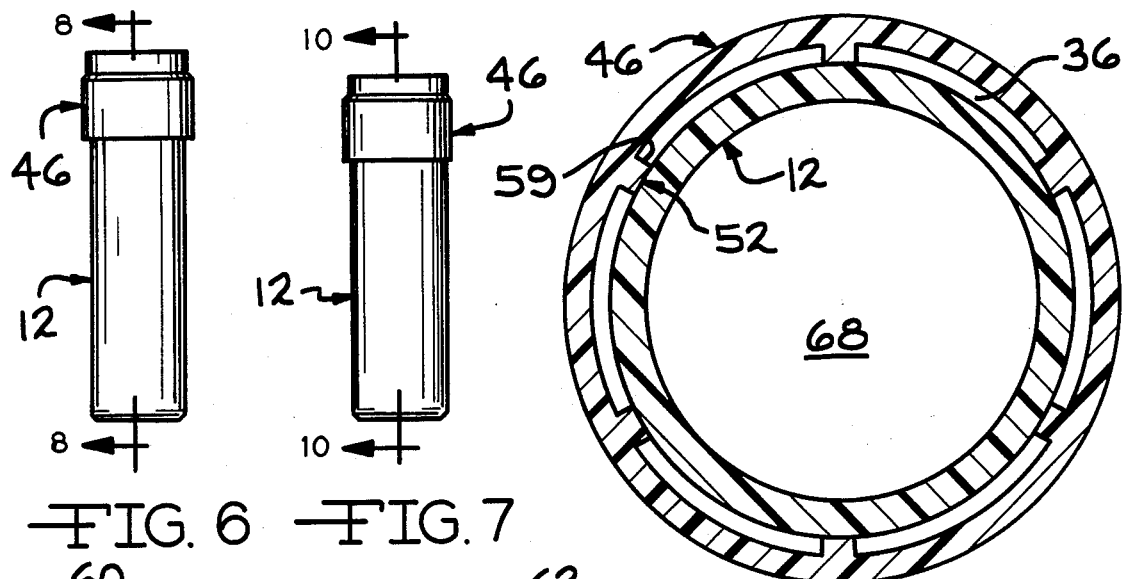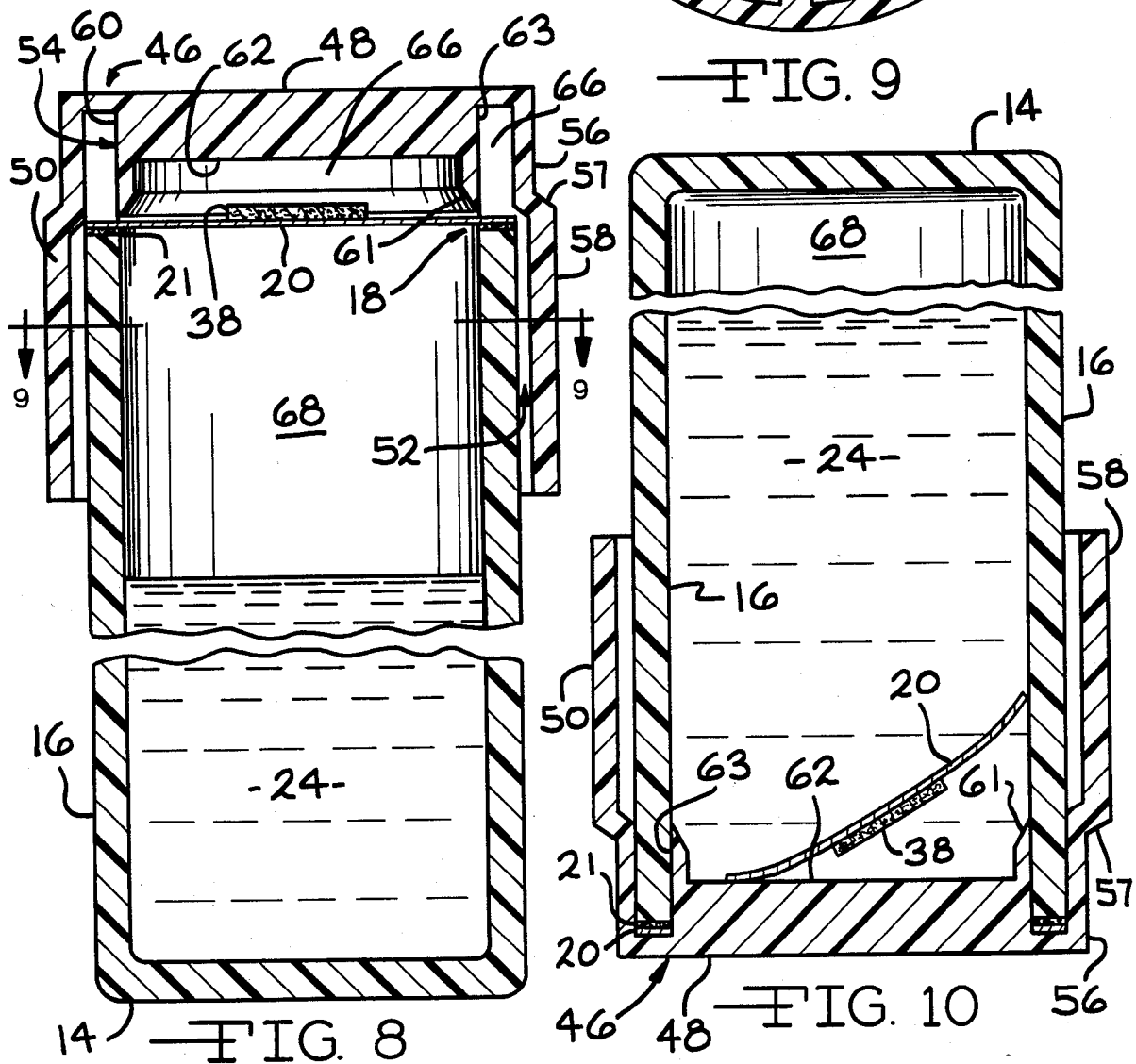

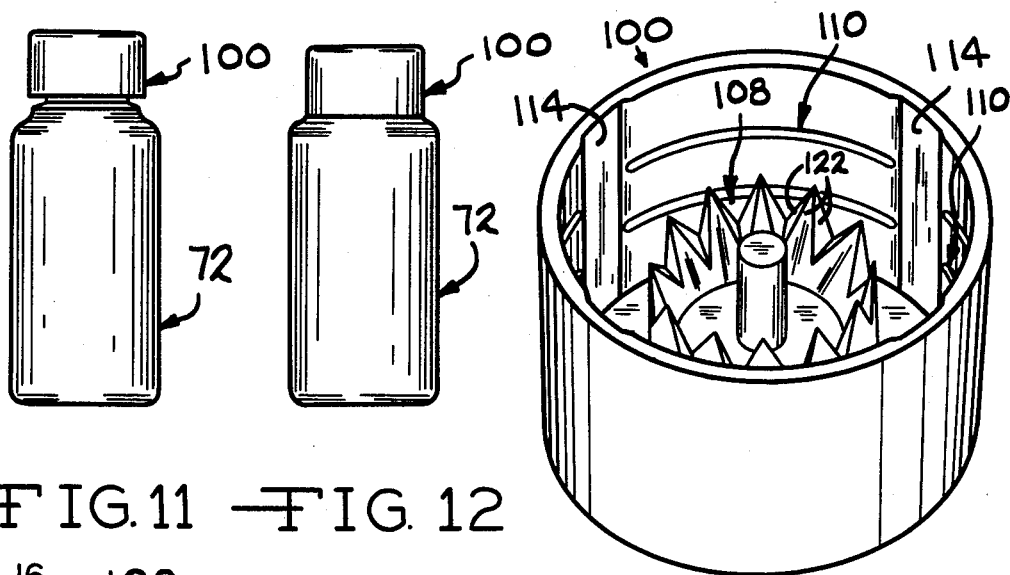
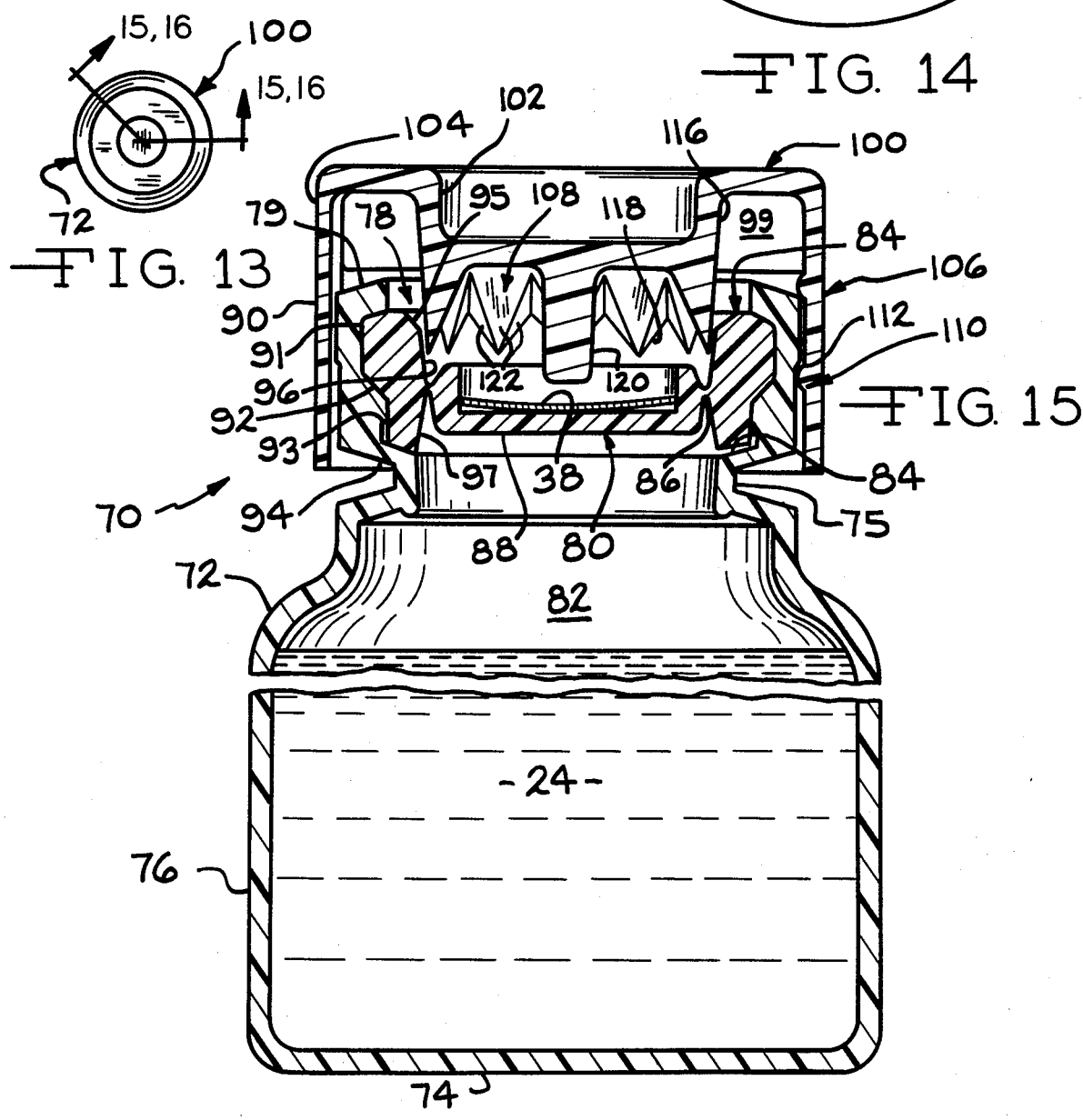

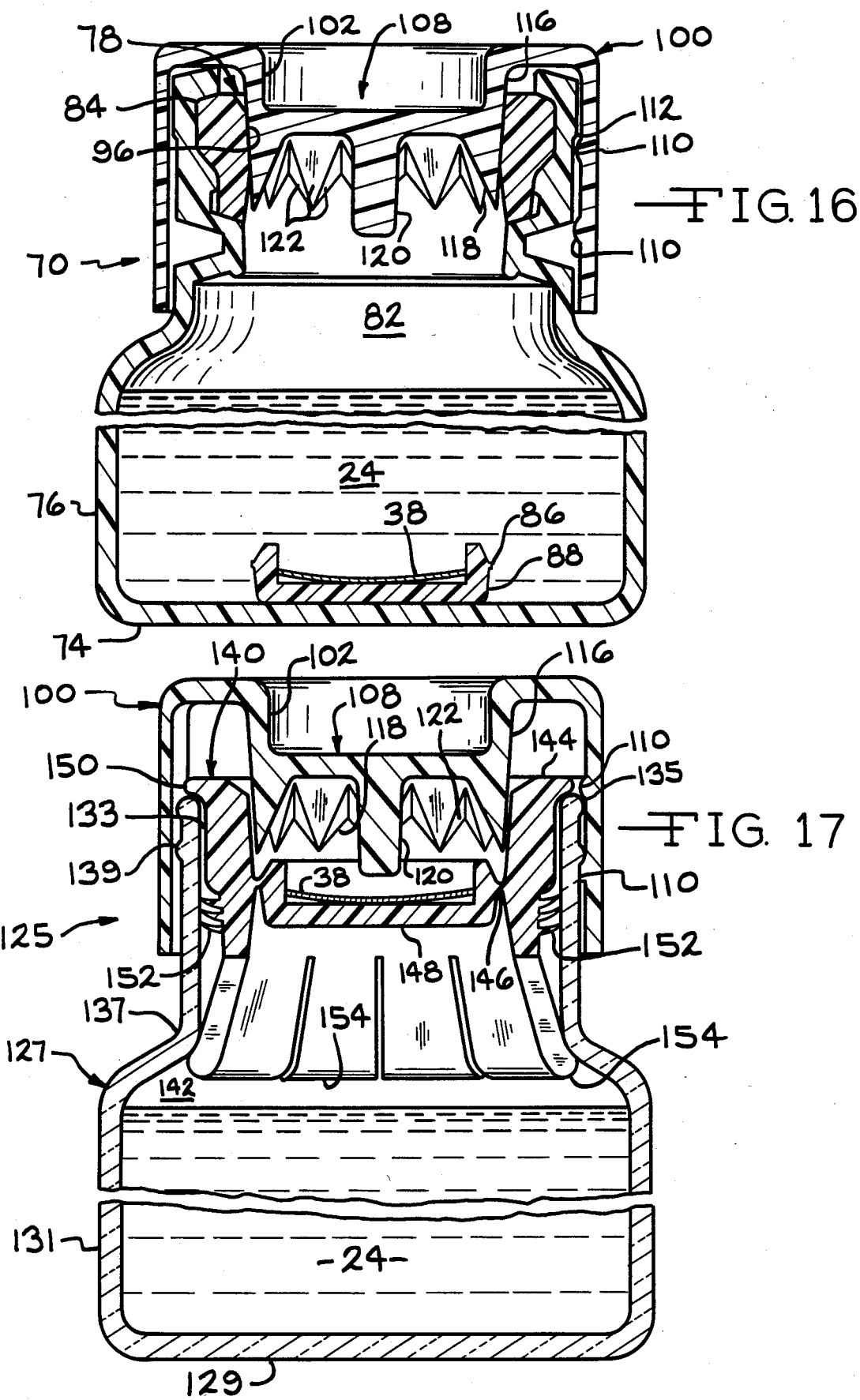

SELF-CONTAINED INDICATOR DEVICE

This patent application is a continuation-in-part of the U.S. patent application, Ser. No. 462,516 filed Jan. 31, 1983, now U.S. Pat. No. 4,580,682.

BACKGROUND OF THE INVENTION

The invention is directed to a self-contained apparatus for use in determining the presence or absence of a biological or chemical substance within a test environment. Prior art tests for determining, for example, the presence of chemical substances or micro-organisms in water and air or the effectiveness of steam or gas sterilization equipment typically require rigid standardized procedures which can only be performed by highly qualified personnel.

A common test for sterilization effectiveness is performed by a technician who first places an absorbent paper test strip which is impregnated with a predetermined number and species of live micro-organisms in a sterilization chamber along with certain objects to be sterilized. The test strip and the objects are then subjected to a sterilization medium such as steam, gas or radiation. Once the sterilization cycle is completed, the technician removes the test strip from the sterilization chamber and places it in a sterile culture medium. The micro-organisms on the test strip are then incubated in the culture medium for a predetermined period of time. The technician then examines the medium to determine whether any micro-organisms on the test strip survived sterilization. Any observable change in color, appearance or turbidity etc., of the medium may indicate that sterilization was not successful.

This above-described sterility test can only be carried out by a skillful technician who is capable of avoiding contamination of the test strip during the various manipulative steps of the test. Similarly, other known tests for the presence or absence of a chemical or biological substances in a test medium requiring the manipulation of a test article require skill to avoid contamination of the test article during the test procedure.

The present invention is a self-contained test apparatus which eliminates potentials for contamination during the test procedure described above. The invention also presents solutions to shortcomings encountered by self contained test apparatus known to applicants;

U.S. Pat. No. 3,440,144, assigned to H. W. Anderson Products, Inc., relates to a package containing a spore strip, a frangible ampule containing a culture medium, a flexible sleeve, and a flexible semi-permeable bag. The frangible ampule has an open spout connected to the body of the ampule by a neck. Sterile culture medium is placed within the ampule through the opening in the spout. The spout is heat sealed, forming a closed ampule. The ampule is then sterilized and placed within the flexible sleeve along with the spore strip. The sleeve is then placed within the flexible bag and the ends of the bag are heat sealed. The bag is then placed in the sterilization chamber along with the objects to be sterilized. Once the sterilization cycle is completed the technician removes the bag from the chamber, grasps the sleeve containing the ampule and spore strip through the bag, and breaks the spout off at the neck of the ampule releasing the culture medium but avoiding tearing the sleeve and the bag with the shards of the ampule. The bag is placed in an incubator for a predetermined period of time. The technician then examines the medium to determine whether any micro-organisms survived the sterilization cycle. The technician must use care throughout this test in order not to prematurely break the ampule or rupture the flexible, semi-permeable bag. A further disadvantage, not dependent upon the skill of the technician, is apparent in using this sterility test. During the sterilization cycle, the sterilant permeates the bag and kills the micro-organisms. However, not all the sterilant passes through the bag. The bag entraps and retains some of the sterilant. After the bag is removed from the sterilization chamber the sterilant continues to diffuse from the bag into the culture medium. The additional sterilant in the culture medium may inhibit and kill the growth of any micro-organisms that have survived the sterility test. Thus, there is a danger that the test apparatus will show a false sterility result.

The U.S. Pat. No. 3,440,144 also relates to a flexible permeable bag sealed at both ends. Culture medium is sealed in one end of the bag and a spore strip is sealed in the other end of the bag. The bag is placed in the sterilization chamber along with the objects to be sterilized. After the sterilization cycle is completed the technician removes the bag from the chamber and squeezes the end of the bag containing the culture medium. The culture medium is forced into the end of the bag containing the spore strip. The bag is then placed in the incubator for a predetermined time, and observed for signs of micro-organism growth. A disadvantage to this test is that the bag does not provide for the direct exposure of the spore strip to the sterilant when the bag is in the sterilization chamber. The bag acts as a shelter for the micro-organisms and may allow some of the micro-organisms to survive the sterility test.

The U.S. Pat. No. 3,661,717, assigned to the Minnesota Mining and Manufacturing Company, and marketed as "ATTEST", relates to a sterility indicator containing a spore strip, a frangible ampule containing a culture medium, a flexible tube, and a gas permeable cap. The spore strip and the ampule are placed in the tube. The ampule fits snugly within the tube such that very little of the volume of the tube is unoccupied. The gas permeable cap is placed over the open end of the tube. The tube is then placed within the sterilization chamber along with the objects to be sterilized. Once the sterilization cycle is completed the technician removes the tube from the sterilization chamber and pinches the tube between the thumb and forefinger crushing the ampule and releasing the culture medium onto the spore strip. The tube is then placed in an incubator for a predetermined time and observed for signs of micro-organism growth. A disadvantage to this prior art is that the cap does not provide for direct exposure of the spore strip to the sterilant when the tube is in the sterilization chamber. Some of the micro-organisms are sheltered and may survive the sterilization. The survival of micro-organisms after the sterilization cycle indicates that the other objects in the chamber were not completely sterilized. When the sterilant does not penetrate through the cap sufficiently to kill the micro-organisms and micro-organisms survive, a false indication of non-sterility results. Another disadvantage to this prior art product is that the lack of a real seal causes the medium to leak through the gas permeable cap after the ampule has been crushed.

The U.S. Pat. No. 4,304,869 and marketed as "PROOF" by American Sterilizer Company, Inc., includes a spore disc, a glass ampule containing a culture medium, a tube having one open end, and a cap containing downwardly extending legs. The spore disc and the ampule are placed within the tube. The ampule fits snugly within the tube. The cap rests on the open end of the tube. The legs on the cap extend into the tube and abut the top of the ampule. The tube is then placed within the sterilization chamber along with the objects to be sterilized. Once the sterilization cycle is completed the technician removes the tube from the sterilization chamber and pushes the cap down on the tube. The legs on the cap exert a force and crush the ampule releasing the culture medium onto the spore disc. The product is then placed in an incubator for a predetermined time and observed for signs of micro-organism growth. However, since the legs on the cap must be long and thick enough to have sufficient force to crush the ampule, the tube must be long in comparison to the length of the legs.

Another prior art product, European patent application No. 78,112, assigned to the American Sterilizer Company relates to a sterilization indicator containing a rigid plastic container holding a spore strip, a breaking wire and a frangible ampule holding a liquid nutrient medium and a dye to indicate any spore growth, and a cap. The spore strip is located at the bottom of the container along with the breaking wire. The frangible ampule fits snuggly within the container and rests on the breaking wire. A cap is positioned over the top of the container and defines an access path to the exterior so that the sterilant cannot enter the container. The container and cap are placed in the sterilization chamber along with the objects to be sterilized. Once the sterilization cycle is completed a technician removes the container from the sterilization chamber and moves the cap in a direction towards the ampule. A central recess portion on the cap exerts a force and crushes the ampule releasing the culture medium onto the spore disc. The container is then placed in an incubator for a predetermined time and obsered for signs of microorganism growth.

In the above described prior art products, the spore strips tend to settle or are deliberately placed at the bottom of the tube and become lodged between the lower closed end of the tube and the lower end of the frangible ampule. The close adjacent relationship of the spore disc with the bottom portions of the tube and ampule cause a "dew point" factor, when the tube is exposed to the sterilization process. The "dew point" factor, caused by the formation of condensation at the bottom of the tube adjacent the lower end of the ampule, prevents the sterilant from effectively reaching and killing these spores on the spore disc.

Other disadvantages of the prior art products are that the sealed ampule is broken and the fluid medium flows into the tube to contact the spore disc. The imperfectly sealed containers permit spillage of the culture medium. The spillage may result in the spreading of the contaminated culture medium. Also, the ampules of the prior art products contain a small volume of culture medium such that, when the prior art product is placed in the incubator, the elevated temperatures of the incubator enhance evaporation of the culture medium. The volume of culture medium is so small that the culture medium evaporates before incubation is complete. Thus, the prior art product may be dried out unless it is placed in a humidified incubator. In addition, the spore carrier in the prior art products is positioned immediately adjacent the ampule in the tube. When the prior art product is placed in the sterilization chamber the ampule acts as a thermal insulator for the spore carrier. Some of the micro-organisms are protected from the sterilant and may survive sterilization.

Accordingly, there is a need in the art for a sterilization indicator which is capable of withstanding high temperature and pressure environments and which indicator device moves a test article from an open chamber into a sealed chamber containing a fluid medium while maintaining the sealed chamber in a sealed condition.

There is a further need for an indicator device wherein an open chamber containing the test article is external to the sealed chamber wherein the outside environment can enter the open chamber and contact the test article such that an adequate exposure to a sterilant is achieved and yet the sterilization does not enter the sealed chamber.

There is a further need for a sterilization indicator which defines a means for moving the test article from an open chamber into a sealed chamber and wherein the sealed chamber remains sealed at all times thereby preventing inadvertant contamination or leaking of the fluid medium from the sealed chamber.

SUMMARY OF THE INVENTION

The invention is directed to a test vial which consists of a container having substantially transparent walls and an initially open end, a barrier seal member for closing the open end of the container and confining within the container a measured quantity of culture medium, and a closure for the container.

The closure and container have cooperating retaining means for holding the closure in place on the container in a first position with the closure telescoped over the end of the container. In this first position the closure and the container define an open chamber that is isolated from the culture medium by the barrier seal member. In one embodiment of the invention, there is a measured number of selected viable bacterial spores on a cotton swab or filter paper carrier in the open chamber.

There are openings connecting the chamber to the atmosphere when the closure is in the first position on the container end. The retaining means may be overcome by moving the closure to a second position in which the closure is telescoped farther onto the end of the container.

The closure has an interior, axially extending portion which penetrates the barrier seal thus placing the spores in the culture medium when the closure is moved axially to the second position. The closure and container can have cooperating means for retaining the closure in such second position.

One advantage of the present invention is that the sealed chamber remains sealed throughout the use of the indicator device so that there is no inadvertent contamination or spillage of the culture medium.

It is an object of the present invention to provide an improved self-contained indicator device which is capable of withstanding high temperature and pressure environments and which device is relatively easy to use for an unskilled person or technician in a laboratory.

Other objects, as well as aspects and advantages, or the present invention will become apparent from the invention as described below.

BRIEF DESCRIPTION OF THE DRAWINGS

FIG. 1 is an elevation view of a first embodiment of the invention in a first position.

FIG. 2 is an elevation view of the embodiment shown in FIG. 1 in a second position.

FIG. 3 is a view taken along the line 3—3 in FIG. 1.

FIG. 4 is a view taken along the line 4—4 in FIG. 3.

FIG. 5 is a fragmentary view taken along the line 5—5 in FIG. 2.

FIG. 6 is an elevation view of a second embodiment of the invention in a first position.

FIG. 7 is an elevation view of the embodiment shown in FIG. 6 in a second position.

FIG. 8 is a view taken along the line 8—8 in FIG. 6.

FIG. 9 is a view taken along the line 9—9 in FIG. 8.

FIG. 10 is a view taken along the line 10—10 in FIG. 7 showing the invention in an inverted position.

FIG. 11 is an elevation view of a third embodiment of the invention in a first position.

FIG. 12 is an elevation view of the embodiment shown in FIG. 11 in a second position.

FIG. 13 is a plan view of the invention shown in FIGS. 11 and 12.

FIG. 14 is a perspective view of a closure of the embodiment shown in FIG. 11.

FIG. 15 is a view taken along the line 15—15 in FIG. 13.

FIG. 16 is a view taken along the line 16—16 in FIG. 13 showing the embodiment in a second position.

FIG. 17 is an elevation view, in cross-section, of a fourth embodiment of the invention.

DESCRIPTION OF THE PREFERRED EMBODIMENTS

Figure 18:
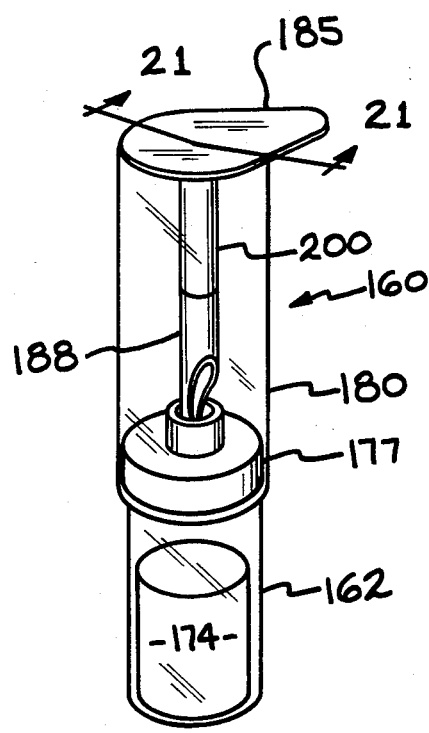
FIG. 18 is a perspective view of a fourth embodiment of the invention in a first position.

The invention is directed to a test vial for use in detecting the presence or absence of a substance in an environment to be tested. Referring to FIGS. 1-5, the test vial 10 generally consists of an initially open container 12, a barrier means 20, and a cap or closure 26. The container 12 is shown as being substantially cylindrical in shape, but it should be understood that other shapes can be used without departing from the scope of the invention. The container 12 can be made from any generally translucent material, including glass or a plastic material such as a polypropylene material. The volume of the container 12 is defined by the capacity requirements of the test for which it is to be used, as will be explained below.

The container 12 generally has a closed end 14, side walls 16, and an open end 18. The open end 18 is closed by a barrier 20. The barrier 20 comprises an impermeable material, such as metal foil or a plastic material as, for example, polypropylene. The barrier 20 can be attached to the container 12 by sealing 21, including an adhesive material.

The barrier 20, the side walls 16 and the closed end 14 of the container 12 define a sealed chamber 22. The barrier 20 acts to confine within the sealed chamber 22 a measured quantity of a fluid medium 24. The fluid medium 24 can comprise any fluid material, including a liquid bacterial culture medium, such as a tryptic soy broth, or a gaseous chemical indicator. The fluid medium 24 is isolated from any external environment by the sealed chamber 22.

The closure or cap 26 is positioned adjacent the open end 18 and the barrier 20 of the container 12. The closure 26 is constructed to axially fit around the open end 18 of the container 12. The closure 26 can be made of any substantially hard material, including a hard plastic material such a polycarbonate or a hard elastomeric material such as a neoprene. The closure 26 includes a top portion 28, a side wall 30, a retaining portion 32, and a detaching element 34.

The closure 26 is positioned adjacent the open end 18 such that the side wall 30 extends from the top portion 28 in a direction towards the closed end 14 of the container 12. The top portion 28, the side wall 30 and the barrier 20 define an open chamber 36. The open chamber 36 is in communication with any outside environment.

A test article 38 is placed within the open chamber 36. The test article 38 can rest on the barrier 20. The test article 38 comprises any suitable material such as an absorbent material such as filter paper or cotton which may be impregnated with spores or a chemical reactant, liquid or solid.

The closure 26 is held in a first position by the retaining means 32. As shown in FIGS. 1-5, the retaining means 32 consists of a plurality of longitudinally extending ribs 40 positioned on the interior side of the side wall 30. The ribs 40 frictionally engage the exterior of the side wall 16 of the container 12. A gas permeable tape (not shown) can be positioned around the closure 26 and the container 12 at the point where the side wall 30 of the closure 26 terminates. The gas permeable tape (not shown) provides a selective barrier against the environment to the open chamber 36 if the particular test so requires.

The detaching means 34 axially extends from the top portion 28 of the closure 26 in a direction towards the barrier 20. The detaching means 34 of the first embodiment of the invention, as shown in FIGS. 1-5, has a frustoconical shape and includes a base 42 and a sloped surface 44. The sloped surface 44 extends from the top portion 28 of the closure 26 at an acute angle such that the area of the base 42 is smaller than the area defined by the open end 18 of the container 12.

The operation of the test device of the invention is as follows: If for example, the test vial 10 is employed in the performance of sterility tests, the test article 38 comprises a strip of porous paper impregnated with spores or other micro-organisms. The medium 24 is a growth medium, such as typtic soy broth, and may have a chemical indicator, such as phenol red. Referring to FIG. 3, the test vial 10 is in its first, ready position for use in a particular test such as a sterility test. The sterility test is conducted with the test vial 10 of the invention by placing the test vial 10 in a sterilization chamber along with objects to be sterilized. The test vial 10 and the objects are exposed to a sterilant such as steam, ethylene oxide or radiation. The sterilant enters the open chamber 36 and contacts the test article 38. The sterilant does not penetrate the barrier 20 or enter the sealed chamber 22. If sterilization is complete, the sterilant kills the organisms on the test article 38.

After the test vial 10 is removed from the tested sterilization chamber, manual pressure is applied to the top portion 28 of the closure 26. The closure 26 is axially moved in a direction towards the barrier 20. As the closure 26 telescopes on the container 12 the base 42 of the detaching means 34 comes into contact with the test article 38 and the barrier 20. As further pressure is applied the detaching means 34 acts to break the barrier 20. The barrier 20 and test article 38 are driven into the sealed chamber 22 and fall into the medium 24. As the closure 26 is further telescoped on the container 12 the sloped surface 44 of the detaching means 34 comes into contact with the open end 18 of the container 12 forming a seal.

The test vial 10 is incubated at optimal temperatures and the medium 24 is observed to find signs of bacterial growth. The signs of bacterial growth would be evidenced by turbidity of the medium 24 or color changes in the chemical indicator. The translucence of the container 12 aids in determining the end points of the test.

Another use of the test vial 10 includes the sampling of a water environment for the presence of a particular chemical or organism. The test vial 10 is submerged in the water environment. The water enters the open chamber 36 and contacts the test article 38. When employed as a water test device the test article 38 is a substantially sterile strip of filter paper. After the test article 38 is saturated with the water and whatever chemicals or organisms are present in the water, the test vial 10 is removed from the water environment. The closure 26 is moved to the second position injecting the test article 38 into the sealed chamber 22. The sealed chamber 22 contains a medium 24 which indicates the presence of a specific chemical or organism.

In FIGS. 6-10 a second embodiment of the invention is shown. The closure 46 includes a top portion 48, a wall 50, retaining means 52 and detaching means 54. The wall 50 has a first section 56, as shown in FIGS. 8 and 10, which extends perpendicularly from the top portion 48. A second section 57 of the wall 50 extends from the first section 56 at an acute angle away from the container 12. A third section 58 extends from the second section 57 in a plane parallel to the first section 56. The retaining means 52 includes a plurality of longitudinally extending ribs 59 which are positioned on the interior surface of the third section 58 of the wall 50. The retaining means 52 acts to hold the closure 46 in a first position.

The detaching means 54 axially extends from the top portion 48 in a direction toward the barrier 20. The detaching means 54 includes a depending annular skirt 60, an edge 61, and a base 62. The depending annular skirt 60 extends perpendicularly from the top portion 48 and is parallel to the first section 56 of the wall 50. The annular skirt 60 extends beyond the base 62 of the detaching means 54. The leading edge 61 of the skirt 60 is wedge-shaped. When the closure 46 is in the first position, an open chamber 66 is formed by the base 62, the barrier 20 and the sections 56, 57, 58 of the wall 50.

In operation, manual pressure is applied to the top portion 48 of the closure 46. As the closure 46 telescopes on the container 12, the wedge-shaped edge 61 comes into contact with the barrier 20. As further pressure is applied the edge 61 ruptures the barrier 20 causing the barrier 20 and the test article 38 to fall into the sealed chamber 68 and into the medium 24. The exterior side 63 of the skirt 60 comes into frictional engagement with the interior of the side wall 16 of the container 12.

The exterior of the side wall 16 comes into frictional engagement with the interior side of the first section 56 of the wall 50 of the closure 46. As the closure 46 telescopes on the container 12 and as the open end 18 comes into contact with the top portion 48 a seal is formed, as shown in FIG. 10.

In FIGS. 11-16 a third embodiment of the invention is shown. The test vial 70 includes an initially open container 72, a barrier 80, and a closure 100. The container 72 generally has a closed end 74, side walls 76, and an open end 78. The open end 78 has a lip 79 which extends radially inward at an acute angle. The container 72 can also have a neck 75 which is positioned adjacent the open end 78. The circumference of the neck 75 is smaller than the circumference of the open end 78.

The barrier 80 is positioned between the neck 75 and the lip 79 of the open end 78. The barrier 80 can be made of any substantially impermeable, rupturable material. In a preferred embodiment the container 72 and the barrier 80 comprises an integrally molded polypropylene vial whose side wall 76, closed end 74 and barrier 80 define a sealed chamber 82. The barrier 80 is defined by an annular sealing member 84, a frangible support membrane 86 and a test article support 88. The barrier 80 acts to confine within the sealed chamber 82 a measured quantity of the fluid medium 24.

The annular sealing member 84 is positioned immediately adjacent the interior of the side wall 76. The sealing member 84 is positioned between the lip 79 and the neck 75 of the open end 78. The sealing member 84 can have exterior sides 90, 91, 92, 93 which matingly engage the interior of the side wall 76. The exterior sides 90, 91, 92, 93 act to form a tight seal with the wall 76 of the container 72.

The sealing member 84 has interior sides 95, 96 and 97. The interior side 95 is positioned at an acute angle to the exterior side 90. The interior side 95 is disposed at such an angle to facilitate the movement of the outside environment through the open chamber 99. The sealing member 84 can have a interior side 95 which is disposed at a greater angle (not shown) to increase the movement of the environment through the open chamber 99.

The membrane 86 is positioned between the interior sides 96 and 97. The membrane 86 extends radially towards the test article support 88. The membrane 86 is sufficiently thin such that it may be easily punctured or ruptured. The membrane 86 must also be thick enough to hold the test article support 88 in position. The test article support 88 is held in position in substantially the center of the open end 78 of the container 72 by the membrane 86. In a preferred embodiment the test article support 88 is shown as having a dish shape. The test article 38 is positioned on the test article support 88. The dish shape of the test article support 88 allows the test vial 70 to be used without a test article 38. The sample of the environment can be collected in the dish shaped surface of the support 88.

The closure 100 is positioned adjacent the open end 78 and the barrier means 80 of the container 72. The closure 100 is constructed to axially fit around the open end 78 of the container 72. The closure 100 can generally be made of any substantially hard material. In a preferred embodiment the closure 100 is made of a polycarbonate material.

The closure 100 includes a top portion 102, side walls 104, retaining means 106, and detaching member 108. The closure 100 is positioned adjacent the open end 78 such that the side wall 104 extends from the top portion 102 in a direction towards the closed end 74 of the container 72.

The top portion 102, the side wall 104 and the barrier 80 define the open chamber 99. The open chamber 99 is in communication with the outside environment. The closure 100 is held in a first position by the retaining ribs 106. The retaining ribs 106 includes a plurality of ridges 110 on the closure 100 and a detent 112 on the closure container 72. The ridges 110 are positioned on the interior side of the wall 104. The ridges 110 radially extend inward. The ridges 110 define a plurality of recesses 114, as best seen in FIG. 14, on the interior of the side wall 104. The recesses 114 allow the environment to flow into the open chamber 99.

The detent 112 is positioned on the exterior side of the container 72. The detent 112 is adjacent the open end 78 of the container 72. The ridges 110 and detent 112 act to hold the closure 100 in frictional engagement against the lip 79 of the container 72 when the closure 100 is in the first position.

Detaching member 108 extends axially from the top portion 102 of the closure 100 in a direction towards the barrier 80. The detaching member 108 includes a depending annular skirt 116, a leading edge 118 and a contact member 120. In a preferred embodiment, the detaching member 108 can be positioned substantially closer to the barrier 80 for ease of manufacturing.

The depending annular skirt 116 extends from the top portion 102 at a slight angle. The angle of the depending skirt 116 is complementary to the angle of the interior side 96 of the sealing member 84 of the barrier 80. The leading edge 118 is positioned at the end of the skirt 116 that is nearest the barrier 80. The leading edge 118 contains a plurality of cutting surfaces 122. In a preferred embodiment the cutting surfaces 122 are positioned to form individual wedges or teeth, as shown in FIGS. 15-17.

The contact member 120 extends axially from substantially the center of the top portion 102 of the closure 100 in a direction towards the barrier 80. The contact member 120 extends beyond the leading edge 118. The contact member 120 can have a substantially cylindrical shape.

In operation, manual pressure is applied to the top portion 102 of the closure 100. As the closure 100 telescopes on the container 72, the contact member 120 strikes the test article 38 and the middle of the test article support 88. As further pressure is applied, the contact member 120 pushes against the test article support 88 and stretches the membrane 86. The depending annular skirt 116 comes into sliding engagement with the interior side 96 of the sealing member 84. The leading edge 118 and the cutting surfaces 122 come into contact with the membrane 86. As further pressure is applied the leading edge 118 and the cutting surfaces 122 puncture the membrane 86. The skirt 116 moves along the interior side 96 and forms a seal with the test article support 88. As the closure 100 continues to telescope on the container 72 the leading edge 118 and the cutting surfaces 122 rupture the membrane 86 causing the test article support 88 and the article 38 to fall into the sealed chamber 82 and into the fluid medium 24.

In this embodiment the container 72 may be made of glass. In a preferred embodiment of the invention the test vial 70 may be formed by a blow mold process. In the blow mold process the container 72 is formed, filled with the fluid medium 24, and sealed with the barrier 80 in a continuous process. The container 72 can be stored for long periods of time. The container 72, the test article 38, and the closure 100 can be assembled at a later point in time. The container 72 and the barrier 80 can be made of a substantially translucent, moldable plastic material such as polypropylene. The closure 100 can be made of a plastic material that will retain a sharp edge, such as a polycarbonate material. In addition, the polycarbonate closure 100 can be color-coded to aid in the identification of the particular test article 38 and fluid medium 24 being used.

In FIG. 17 a fourth embodiment of the invention is shown. The test vial 125 includes the closure 100 of the third embodiment, an initially open container 127, and a barrier 140. The container 127 generally has a closed end 129, side walls 131, and an open end 133. The open end 133 has a lip 135 which extends radially outward. The container 127 has a neck 137. The neck 137 has a circumference which is smaller than the circumference of the sealed chamber 142. In this embodiment the container 127 can be made of glass.

The barrier 140 is positioned adjacent the open end 133 and the lip 135 of the container 127. The barrier 140, the side wall 131 and the closed end 129 of the container 127 define a sealed chamber 142. The barrier 140 acts to confine within the sealed chamber 142 a measured quantity of the fluid medium 24. The barrier 140 has an annular sealing member 144, a membrane 146 and a test article support 148.

The annular sealing member 144 is positioned adjacent the interior of the side wall 127. The sealing member 144 has a lip 150, at least one fin 152 and a plurality of flanges 154. The lip 150 radiates outwardly and is positioned adjacent the lip 135 of the container 127. The lip 150 acts to hold the barrier 140 in position on the open end 133 of the container 127. The fin 152 extends from the exterior side of the sealing member 144 in a direction towards the side wall 131 of the container 127. The fin 152 can extend radially towards the side wall 131 of the container 127. Alternatively, the fin 152 can extend in a downward direction (not shown) towards the side wall 131. The fin 152 acts to form a seal when the barrier 140 is positioned in the open end 133 of the container 127.

The plurality of flanges 154 extends from the sealing member 144 in a direction towards the neck 137 of the container 127. The lower portion of the flanges 154 defines a circumference greater than the circumference of the neck 137. The flanges 154 are flexible such that the barrier 140 can be easily inserted into the container 127. The flanges 154 act to hold the barrier 140 in position in the container 127.

When the closure 100 is in the second position, (not shown) the ridges 110 of the closure 100 engage a ridge 139 on the container 127. The ridge 139 extends radially from the exterior of the side wall 131. The ridge 139 extends substantially around the exterior of the side wall 131 such that the ridges 110 engage the ridge 139 at all times when the closure 100 is in the second position.

In FIGS. 18-23 a fifth embodiment of the test vial of the present invention is shown. The test vial 160 generally consists of an initially open container 162, a barrier seal 170 and a cap or closure 180. The container 162 is shown as being substantially cylindrical in shape, but it should be understood that other shapes can be used without departing from the scope of the invention. The container 162 can be made of any generally transparent or translucent material, including glass or a plastic material. The volume of the container 162 is defined by the capacity requirements of the test for which the test vial is to be used.

The container 162 generally has a closed end 164, side walls 166 and an open end 168. The open end 168 has a lip 169 which extends radially outwardly from the opening 168. The container 162 can also have a neck 165 which is positioned adjacent the open end 168. The circumference of the neck 165 is generally smaller than the circumference of the container 162. The open end 168 is closed by the barrier seal 170. The barrier seal 170 comprises an impermeable material, such as butyl rubber. The barrier seal 170, the side walls 166 and the closed end 164 of the container 162 define a sealed chamber 172. The barrier seal 170 acts to confine within the sealed chamber 172 a measured quantity of a fluid medium 174. The fluid medium can comprise any material, including a liquid bacterial culture medium, such as a tryptic soy broth or a gaseous chemical indicator. The fluid medium 174 is isolated from any external environments by the sealed chamber 172.

In a preferred embodiment the barrier seal 170 has a core or central portion 171 which extends in an axial direction downwardly into the open end 168 of the container 162 and a lip 173 which extends radially outwardly from a membrane 179. The lip 173 is positioned adjacent the lip 169 of the container 162 when the barrier seal 170 is matingly seated within the open end 168 of the container 162. The lip 173 acts to hold the barrier seal 170 in position on the open end 168 of the container 162. The barrier seal 170 can further include at least one flange or sealing member 175 which extends radially outwardly from the core portion 171 of the barrier seal 170. The flange 173 extends from the side of the core 171 of the barrier seal 170 in a direction towards the side wall 167 of the open end 168. The flange 175 aids in forming a seal when the barrier seal 170 is positioned in the open end 168 of the container 162. The flange 175 is flexible such that the barrier seal 170 can be easily inserted into the container 162. The flange 175 also aids in holding the barrier seal 170 in position in the container 162.

An annular member 176 is positioned immediately adjacent the barrier seal 170. The annular member 176 includes an aperture 179 and a downwardly depending skirt 178 which extends in a direction toward the neck 165 of the container 162. The annular skirt 178 can be crimped over the barrier seal 170 and lip 169 of the container 162 in order to hold the barrier seal 170 in a snug relationship in the open end 168 of the container 162.

The cap or closure 180 is positioned adjacent the barrier seal 170 and the open end 168 of the container 162. The closure 180 is constructed to axially fit around the open end 168 of the container 162. The closure 180 can be made of any substantially hard material, including a hard plastic such as a polycarbonate material. The closure 180 includes a top portion 182, a side wall 184, a penetrating means 188 and a retaining means 190.

Figure 19:
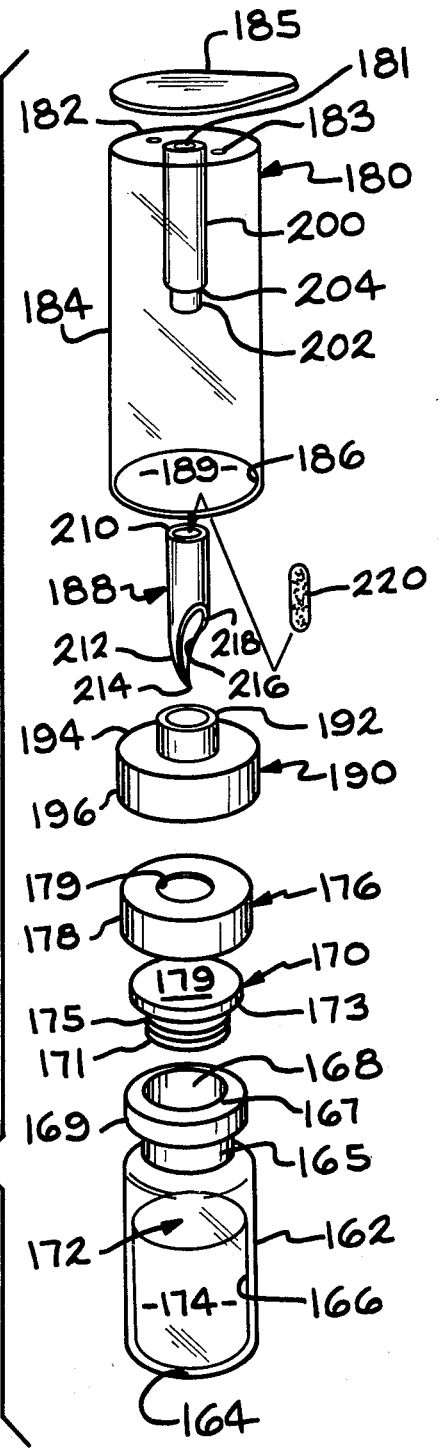
FIG. 19 is an exploded perspective view of the embodiment shown in FIG. 18.
Figure 20:
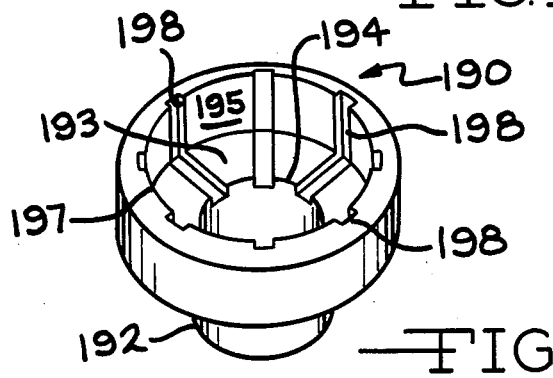
FIG. 20 is a perspective view of a portion of the closure of the embodiment shown in FIGS. 18 and 19.

The closure 180 is positioned adjacent the open end 168 such that the side wall 184 of the closure 180 extends downwardly from the top portion 182 in a direction towards the closed end 164 of the container 162. The top portion 182, the side wall 184, the retaining means 190 and the barrier seal 170 define an open chamber 189. The open chamber 189 is in communication with any outside environment. The closure 180 is held in a first position by a radially inwardly extending detent 186 on the interior side of the side wall 184. The detent 186 matingly engages the exterior of the retaining means 190. The retaining means 190 is coaxially positioned within the closure 180 and is held in position in the closure 180 by an interference fit. The retaining means 190 aids in supporting the closure 180 in a first position and in receiving the closure 180 in a second position. As best shown in FIGS. 19 and 20, the retaining means 190 includes a hollow collar 192, a shoulder 194 which extends perpendicularly from the collar 192 and a depending annular skirt 196 extending perpendicularly from the shoulder 194 and substantially parallel to the collar 192. The retaining means 190 is coaxially positioned over the annular member 176 and the barrier seal 170. As best seen in FIG. 20, the shoulder 192 and the depending annular skirt 194 have interior walls 193, and 195, respectively. The interior walls 193 and 195 define a plurality of longitudinally extending rib members 197 and recesses 198. The rib members 197 of the depending annular skirt 194 frictionally engage the exterior of the side walls of the depending annular skirt 177 of the annular member 176. The recesses 198 are disposed along the interior side walls 193 and 195 of the skirt 194 and shoulder 192 such as to allow the movement of an exterior environment through the recesses 198 and the hollow collar 192 of the retaining means 190 into the open chamber 189.

The closure 180 further includes a contact member 200 which extends axially from substantially the center of the top portion 182 of the closure 180 in a direction towards the barrier seal 170. The contact member 200 defines a base portion 202 which is located at the end of the contact member 200 opposite the end attached to the top portion 182 of the closure 180. The base portion 202 has a generally smaller circumference than the contact member 200 such that a shoulder 204 is defined on the contact member 200. The base portion 202 has an outside diameter which is slightly less than the outside diameter of the penetrating means 188 such that the penetrating means 188 is coaxially positioned adjacent the base portion 202 by the contact member 200, as will be described in detail below.

Figure 21:
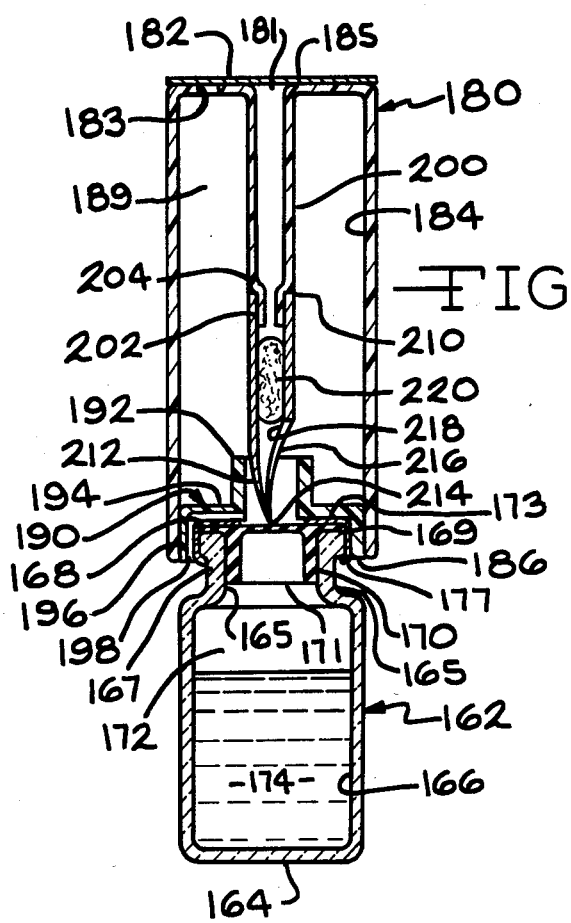
FIG. 21 is an elevation view, in cross-section of the embodiment shown in FIG. 18 in a first position.

As best seen in FIG. 19, the penetrating means 188 has a generally hollow shape and, in the preferred embodiment, is substantially cylindrical. The penetrating means 188 has a first end 210 which is coaxially positioned over the base portion 202 of the contact member 200. The first end 210 is loosely seated against the shoulder 204 of the contact member 200. The penetrating means 188 further includes a second end 212 which is positioned immediately adjacent the barrier seal 170 and rests on the barrier seal 170. As best shown in FIG. 21, the second end 212 is coaxially positioned within the collar 192 of the retaining means 190 and rests on the barrier seal 170. The second end 212 further defines a pointed portion 214 and a leading edge 216. The leading edge 216 has a curved or wedge shape and contains at least one cutting surface 218. In a preferred embodiment the leading edge 216 is curved such that as the second end 212 is moved through the barrier seal 170, the curved leading edge 216 acts to penetrate and yet not tear the barrier seal 170. Further, until the curved leading edge 216 has completely moved through the barrier seal 170, the barrier seal 170 is not broken, as will be described in detail below. A test article 220 is placed within the hollow penetrating means 188. The test article 220 is held within the penetrating means 188 by an interference fit. The test article 220 comprises any suitable material such as an absorbent material made of a filter paper or cotton which may be impregnated with spores or a chemical liquid or a solid.

In a preferred embodiment, the top portion 182 of the closure 180 includes an aperture 181 and at least one aperture 183. The apertures 181 and 183 extend through the top portion 182 such that the exterior environment may enter the open chamber 189 through the apertures 181 and 183. In a preferred embodiment a tab or tape 185, which is permeable to gas but is impermeable to bacteria, is affixed immediately adjacent the top portion 182 of the closure 180. The gas permeable tab 185 can be used to identify the various components of the test vial 160, such as type of fluid medium in the container 162 or species of test indicator on the test article 220, along with the general information regarding the size and volume of such fluids or test indicator.

As shown in FIG. 21, the closure 180 is held in a first position by the interior sides of the side walls 184 and the detent 186 on the closure 180 which are in frictional engagement with the retaining means 190. As shown in FIG. 21, the open chamber 189 is defined by the recesses 198, the collar 192 and the interior of the closure 180.

Figure 22:
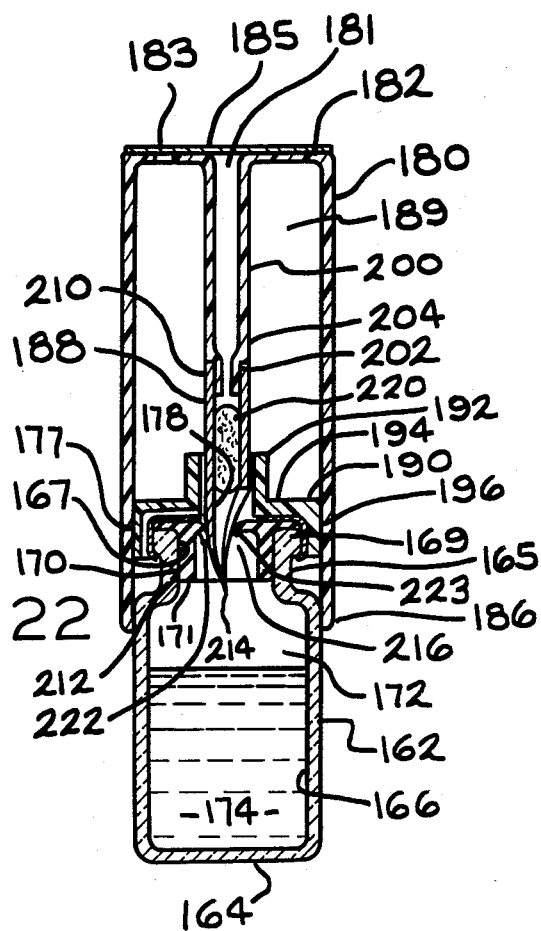
FIG. 22 is an elevation view, in cross-section, of the embodiment shown in FIG. 21 in a second position.
Figure 23:
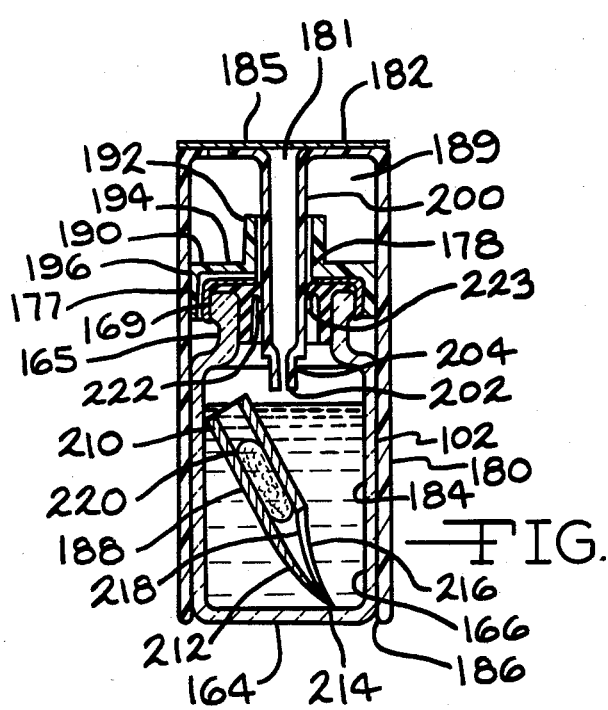
FIG. 23 is an elevation view, in cross-section, of the embodiment shown in FIG. 21 and 22 in a third position.

The operation of the test vial 160 is as follows: if for example, the test vial 160 is employed in the performance of sterility tests, the test article 220 comprises a small portion of a cotton material impregnated with spores or other micro-organisms. The fluid medium 174 is a growth medium, such as tryptic soy broth, and may have a chemical indicator, such as phenol red. Referring to FIG. 21 in particular, the test vial 160 is in its first, ready position for use in a sterility test. The sterility test is conducted with the test vial of the present invention by placing the test vial in a sterilization chamber along with the objects to be sterilized. The test vial 160 and the objects are exposed to a sterilant, such as steam or ethylene oxide. The sterilant enters the open chamber 189 through the recesses 198 and apertures 181 and 183 and contacts the test article 220. The sterilant does not penetrate the barrier seal 170 or enter the sealed chamber 172. If the sterilization is complete, the sterilant kills the micro-organisms on the test article 220. After the test vial 160 is removed from the tested sterilization chamber, manual pressure is applied to the top portion 182 of the closure 180. The closure 180 is axially moved in a direction towards the barrier seal 170. As the closure 180 telescopes on the container 162 the pointed end 214 on the second end 212 of the penetrating means 188 penetrates the barrier seal 170. As further pressure is applied, the curved leading edge 216 and the cutting surfaces 218 on the curved leading edge 216 further penetrate through the barrier seal 170. The penetration of the curved leading edge 216 through the barrier seal 170 causes portions 222 and 223 of the barrier seal 170, as best shown in FIG. 22, to be curved or oriented in a downward direction towards the closed end 164 of the container 162. The curved leading edge 216 guides the second end 212 causing the second end 212 to penetrate the barrier seal 170 without detaching any part of the barrier seal 170. As the closure 180 is further telescoped on the container 162, the penetrating means 188 is moved through the barrier seal 170, and a portion of the contact member 200 is guided through the barrier seal 170. In a preferred embodiment, the barrier seal 170 is made of an elastomeric material such that the portions 222 and 223 of the barrier seal 170 are compressed by the penetrating means 188 and the contact member 200 in a radially outward direction towards the neck 165 of the container 162. Also, as shown in FIG. 22, the detent 186 and the interior sides of the side walls 184 frictionally engage the side walls 166 of the container 162 to aid in forming a seal. As the closure 180 continues to telescope on the container 162, the penetrating means 188, no longer held by the frictional engagement with the portions 222 and 223 of the barrier seal 170, falls into the sealed chamber 172 and into the fluid medium 174. Thus, the test article 220 carried by the penetrating 188 means is moved from the open chamber 189 and injected into the sealed chamber 172 while the sealed chamber 172 is maintained in a sealed condition.

The test vial 160 is then incubated at optimal temperatures and the fluid medium 174 is observed to find signs of bacterial growth or signs of contamination. The signs of bacterial growth would be evidenced by turbidity of the medium 174 or color changes in the chemical indicator. The substantial tranparency of the container 162 and the closure 180 aid in visualizing the end point of the test.

In this embodiment the container 162 may be made of glass and the closure 180 can be made of a substantially hard plastic material such as polycarbonate material. The penetrating means 188 can be made of any hard material which will retain a sharp edge, such as a polycarbonate material or a metal which is non-reactive with the test article 220 and the fluid medium 174.

The above-identified description of the invention is given only for the sake of explanation. Various modifications and substitutions, other than those cited, can be made without departing from the scope of the invention as defined in the following claims.

What we claim is:

1. A test vial, comprising:
   a first liquid impermeable chamber defined by at least one gas imprevious wall and a gas impervious seal member, and filled with a fluid;
   a second chamber defined by at least one wall having an open end adjacent said first chamber and a gas permeable end opposite said open end, said second chamber operatively connected to said first chamber for movement from an open position to a closed position adjacent said gas impervious seal member;
   said second chamber defining an open path from an outside environment through said open end and said gas permeable end of said second chamber;
   an article supported within said second chamber and isolated from said first chamber by said seal member for exposure to said outside environment; and,
   means on said second chamber for penetrating said seal member, moving said article from said second chamber into said first chamber, and maintaining said first chamber in a liquid impermeable condition, thereby sealing said article and said fluid medium within said first chamber.

2. The test vial of claim 1, wherein said penetrating means includes a leading edge, said leading edge being substantially pointed, said leading edge sealing said first chamber in a liquid impermeable condition when said second chamber is moved from said open position to said closed position.

3. The test vial of claim 2, wherein said penetrating means includes a plurality of curved-shaped surfaces, said curved-shaped surfaces penetrating said seal member, moving said article from said second chamber into said first chamber and maintaining said first chamber in a liquid impermeable condition, thereby sealing said article and said fluid medium within said first chamber.

4. The test vial of claim 1, wherein said penetrating means includes at least one pointed member, said pointed member penetrating said seal member, moving said article from said second chamber into said first chamber and maintaining said first chamber in a liquid impermeable condition, thereby sealing said article and said fluid medium within said first chamber.

5. The test vial of claim 1, wherein said seal member is positioned substantially adjacent an interior side of said first chamber, said seal member frictionally engaging said interior side of said first chamber; said seal member further including a membrane member, said membrane member being positioned on said seal member and extending across said first chamber and covering said first chamber, said membrane member being capable of being readily penetrable upon movement of said second chamber from said open position to said closed position.

6. The test vial of claim 1, wherein said article is a test article, said test article being in communication with said outside environment when said second chamber is in said open position, said test article acting to sample or measure a portion of said outside environment.

* * * * *